[19] United States Patent
Bauer et al.
[11] 3,962,259
[45] June 8, 1976

[54] 1,3-DIHYDROSPIRO[ISOBENZOFURAN]S AND DERIVATIVES THEREOF

[75] Inventors: Victor J. Bauer, Somerville; Raymond W. Kosley, Jr., Convent, both of N.J.

[73] Assignee: American Hoechst Corporation, Bridgewater, N.J.

[22] Filed: Dec. 12, 1973

[21] Appl. No.: 424,080

[52] U.S. Cl........................ 260/293.58; 260/326.34; 260/326.5 D; 260/343.3 R; 260/346.2 R; 424/267; 424/274; 424/279; 424/285

[51] Int. Cl.$^2$........................................ C07D 491/10

[58] Field of Search.................. 260/293.58, 326.34, 260/326.5 D, 343.3, 346.2 R

[56] References Cited

UNITED STATES PATENTS 3,686,186 8/1972 Houlihan et al. .............. 260/293.58

OTHER PUBLICATIONS

Braenden et al., Bull. World Health Org. 13, 937 and 956–961 (1955).

*Primary Examiner*—G. Thomas Todd
*Attorney, Agent, or Firm*—Curtis, Morris & Safford

[57] ABSTRACT

Novel substituted 1,3-dihydrospiro[isobenzofuran]s and methods of preparing the same are described. These compounds are useful as tranquilizers, analgetic agents and intermediates therefor.

6 Claims, 1 Drawing Figure

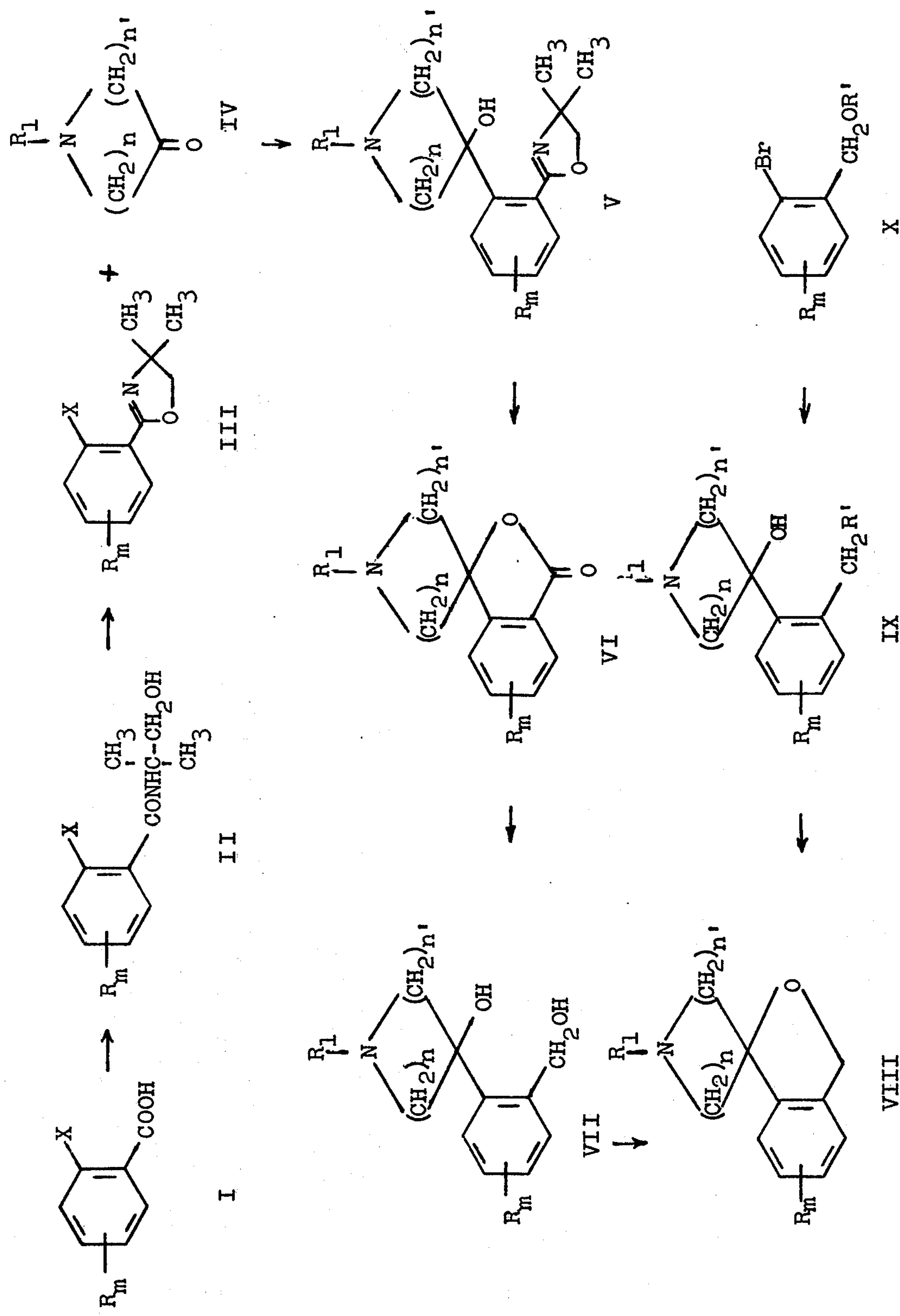
I
II
III
IV
V
VI
VII
VIII
IX
X

1,3-DIHYDROSPIRO[ISOBENZOFURAN]S AND DERIVATIVES THEREOF

This invention relates to novel substituted 1,3-dihydrospiro[isobenzofuran]s which are useful as tranquilizers, analgetic agents and as intermediates therefor, to methods of preparing the same, to methods of treatment with pharmaceutically effective amounts thereof, and to pharmaceutical compositions containing such compounds as essential active ingredients.

To the best of our knowledge, the compounds of this invention have not heretofore been described or suggested. Spiro[phthalan-piperidine]s of the formula

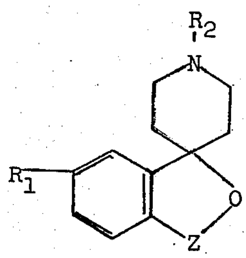

in which $R_1$ is hydrogen, lower alkyl, lower alkoxy, halogen or trifluoromethyl, $R_2$ is hydrogen or benzyl, and Z is —$CH_2$— or —CO—, described by W. J. Houlihan et al. in U.S. Pat. No. 3,686,186, are outside the scope of the invention. The same applies to the natural product of the formula

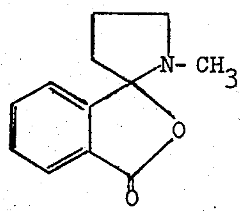

described by Y. Inubushi et al. [Chem. and Pharm. Bull. (Japan), 12, 749 (1964)].

This invention relates to novel substituted 1,3-dihydrospiro[isobenzofuran]s of the formula:

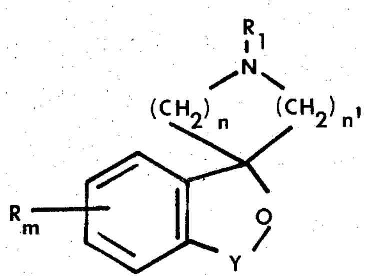

in which

R is hydrogen, alkyl of 1 to 6 carbon atoms, alkoxy of 1 to 6 carbon atoms, trifluoromethyl, halogen, hydroxy or methylenedioxy;

$R_1$ is alkyl of 1 to 6 carbon atoms, cycloalkylalkyl of 4 to 8 carbon atoms, phenylalkyl of the formula $CH_2(CH_2)_nPhR$, diphenylalkyl of the formula $(CH_2)_n$—$CH(PhR)_2$, diphenylmethoxyalkyl of the formula —$(CH_2)_n$—$OCHPh_2$, alkanoyl of 2 to 6 carbon atoms, phenylalkanoyl of the formula —$CO(CH_2)_n$—PhR, benzoyalkyl of the formula —$(CH_2)_n$—COPhR, phenylhydroxyalkyl of the formula —$(CH_2)_n$—CHOH—PhR, or cycloalkylcarbonyl of 4 to 7 carbon atoms;

Y is $CH_2$ or CO;

Ph is phenyl;

$m$ is 1 or 2;

and $n$ and $n'$ are integers from 1 to 3; as well as the pharmaceutically acceptable acid addition salts thereof, e.g., the hydrochlorides, hydrobromides, sulfates, oxalates, fumarates and maleates.

The compounds of this invention can be prepared as described below with reference to the attached drawing in which, with the exceptions noted, R, $R_1$, $R_2$, Y, $m$, $n$ and $n'$ are as defined previously and X is halogen, preferably chlorine or bromine.

Method A

An o-halobenzoic acid I, in which R is hydrogen, alkyl, alkoxy, halogen, trifluoromethyl or methylenedioxy and $m$ is 1 or 2, is converted to the corresponding benzoyl chloride by treatment with a halogenating agent such as thionyl chloride, phosphorus pentachloride, or oxalyl chloride at a temperature of 0° to 120° for a time of 0.25 to 24 hours in the presence or absence of a catalyst such as dimethylformamide with or without a solvent inert to the reactants such as ether, toluene, or dichloromethane. The benzoyl chloride is then allowed to react with 2-amino-2-methyl-1-propanol at a temperature of from −20° to 35° with or without an acid-neutralizing agent such as sodium bicarbonate in the presence of a solvent such as dichloromethane or benzene to provide an o-halo-N-(1-hydroxy-2-methyl-2-propyl)benzamide II. It will be readily appreciated by those skilled in the art that the time and temperature necessary to complete the reaction in this and subsequent steps are interrelated and dependent upon the structures and compositions of the reaction components and the solvent.

The o-halo-N-(1-hydroxy-2-methyl-2-propyl)benzamide II is cyclized to an o-halophenyloxazoline III by treatment with a dehydrating agent such as thionyl chloride, phosgene, or phosphorus oxychloride at a temperature of −20° to 40° in the presence or absence of a solvent such as toluene, pyridine, or chloroform for a time of 0.5 to 24 hours.

The o-halophenyloxazoline III is converted to the Grignard reagent under the usual conditions, i.e. by reaction with magnesium at a temperature of preferably 25° to 100° in a solvent such as ether or tetrahydrofuran for a time of preferably 0.25 to 24 hours with or without the assistance of an initiator such as iodine or 1,2-dibromoethane. Reaction of the Grignard reagent with a cycloazalkanone IV at a temperature of −60° to 100° for a time of 0.25 to 24 hours provides an oxazolinylphenylcycloazalkanol V.

The oxazolinylphenylcycloazalkanol V is treated with an acid such as aqueous hydrochloric or sulfuric acid at a temperature of 25° to 125° for a time of 10 minutes to 24 hours with or without a solvent such as water, ethanol, or acetic acid to provide a 1,3-dihydrospiro[isobenzofuran-cycloazalkane]-3-one VI.

EXAMPLE B

The 1,3-dihydrospiro[isobenzofuran-cycloazalkane]-3one VI is converted by a reducing agent such as lithium aluminum hydride or sodium bis(2-methoxyethoxy) aluminum hydride at a temperature of 0° to 110° in a solvent such as toluene, ether or tetrahydrofuran for a time of 10 minutes to 24 hours to an o-hydroxymethylphenylcycloazalkanol VII.

The o-hydroxymethylphenylcycloazalkanol VII is treated with an acid, such as hydrochloric or o-toluenesulfonic acid, preferably a solvent, such as toluene or acetic acid at a temperature of 25° to 150°, preferably 25° – 110° for a time of 5 minutes to 24 hours, preferably 5 minutes to 3 hours, to provide a 1,3-dihydrospiro[isobenzofuran-cycloazalkane] VIII.

Method C

An o-halobenzyl alcohol X in which R and *m* are defined as in the description of Method A and R′ is hydrogen, is converted to the lithium derivative by treatment with an alkyllithium of preferably 1 to 6 carbon atoms at a temperature of −30° to 100° for a time of 10 minutes to 12 hours in a solvent such as ether, hexane or tetrahydrofuran. Alternatively, an o-halobenzyl ether X (in which R′ is alkyl) is converted to the lithium derivative or Grignard reagent in the usual manner. The resulting lithium o-lithiobenzalkoxide, o-lithiobenzyl ether, or Grignard reagent is allowed to react with a cycoazalkanone IV for a time of 0.25 to 24 hours under reaction conditions which are commonly used for this type of reaction, e.g., at a temperature of −80° to 100°, preferably −80° to 20°, in a solvent such as ether, tetrahydrofuran, or hexane to provide an o-hydroxymethylphenylcycloazalkanol or its ether IX.

The o-hydroxymethylphenylcycloazalkanol or its ether IX is then cyclized to a 1,3-dihydrospiro[isobenzofuran-cycloazalkane] VIII by acid treatment as in Method A, above.

Method D

An N-benzyl-1,3-dihydrospiro[isobenzofurancycloalkanone] VI or cycloazalkane VIII in which $R_1$ is $CH_2PhR$, is hydrogenated at a pressure of 1 to 15 atmospheres with a catalyst such as palladium on carbon in a solvent such as ethanol, acetic acid or water in the presence of an acid such as hydrochloric or perchloric acid at a temperature of 25° to 100° until hydrogen uptake ceases to form the corresponding 1,3-dihydrospiro[isobenzofuran-cycloalkanone] VI or cycloazalkane VIII in which $R_1$ is hydrogen.

Method E

A 1,3-dihydrospiro[isobenzofuran-cycloalkane] VIII in which $R_1$ is hydrogen can be prepared by treating an N-substituted 1,3-dihydrospiro[isobenzofuran-cycloazalkane] VIII with a chloroformate, e.g., an alkyl- or phenylchloroformate, at a temperature of 25° to 125°C. fo 0.25 to 24 hours in a solvent such as toluene or benzene to provide the corresponding N-alkoxycarbonyl- or N-phenyloxycarbonyl-1,3-dihydrospiro[isobenzofuran-cycloazalkane], which is then treated with a base such as sodium or potassium hydroxide in a solvent such as water or ethanol, or with an acid such as hydrogen bromide in acetic acid, for 0.25 to 24 hours at a temperature of 25° to 125°C.

Method F

An N-unsubstituted 1,3-dihydrospiro[isobenzofuran-cycloazalkanone] VI or cycloazalkane VIII prepared by Methods D or E can be reacted in known manner with an alkanoyl chloride or anhydride, aroyl chloride or anhydride, aralkanoyl chloride, alkyl halide, alkenyl halide, cycloalkylcarbonyl halide, aralkyl halide or aroylalkyl halide, to provide the corresponding N-alkanoyl, N-aroyl, N-aralkanoyl, N-alkyl, N-alkenyl, N-cycloalkylcarbonyl, N-aralkyl or N-aroylalkyl derivative.

Method G

The N-alkoxycarbonyl-, N-benzyloxycarbonyl-, N-aryloxycarbonyl-, N-alkanoyl, N-cycloalkylcarbonyl-, N-aroyl, N-aralkanoyl-1,3-dihydrospiro[isobenzofuran-cycloazalkanes] VIII prepared by Methods E and F can be reduced in a known manner with a reagent such as lithium aluminum hydride to the corresponding N-alkyl- or N-aralkyl-1,3-dihydrospiro[isobenzofuran-cycloazalkanes] VIII.

Compounds of the present invention are useful as tranquilizers due to their depressant action on the central nervous system of mammals. This activity is demonstrated in the mouse observation procedure, a standard assay for CNS depressants [Psychopharmacologia, 9, 259 (1966)]. Thus, for instance, the minimum effective dose (MED) at which 1,3-dihydro-1′-[3-(4-fluorobenzoyl)propyl]spiro[isobenzofuran-1,4′-piperidine]-3-one displays significant effects on behavior and reflex depression together with muscle relaxation is 10 mg/kg. Similarly, MED's of other compounds are:

| | MED mg/kg. |
|---|---|
| 1,3-dihydro-1′-methylspiro[isobenzofuran-1,4′-piperidine]-3-one | 37.5 |
| 1,3-dihydro-1′-(2-phenethyl)spiro[isobenzofuran-1,4′-piperidine]-3-one | 18.75 |
| 1,3-dihydro-1′-[4,4-di(4-fluorophenyl)butyl]spiro-[isobenzofuran-1,4′-piperidine]-3-one | 50 |
| 1,3-dihydro-1′-methylspiro[isobenzofuran-1,4′-piperidine] | 50 |

Compounds of the present invention are also useful as analgesic agents due to their ability to alleviate pain in mammals. The activity of the compounds is demonstrated in the 2-phenyl-1,4-quinone-induced writhing assay in mice, a standard assay for analgesia [Proc. Soc. Exptl. Biol. Med., 95, 729 (1957)]. For example, an approximately 50% inhibition of phenylquinone writhing is effected by 1,3-dihydro-1′-methylspiro[isobenzofuran-1,4′-piperidine]-3-one, 1,3-dihydro-1′-[4,4-di(4-fluorophenyl)butyl[spiro[isobenzofuran-1,4′-piperidine]-3-one and 1,3-dihydro-1′-[3-(4-fluorobenzoyl)propyl]spiro[isobenzofuran-1,4′-piperidine]-3-one at doses of 22, 11.5 and 11 mg/kg., respectively. Similarly, 50 mg/kg. doses of 1′-butyl-1,3-dihydrospiro[isobenzofuran- 1,4′-piperidine]-3-one, 1,3-dihydro-5-methoxy-1′-methylspiro[isobenzofuran-1,4′-piperidine]-3-one, and 1,3-dihydro-5-methoxy-1′-methylspiro[isobenzofuran-1,4′-piperidine] exhibit a 37%, 47% and 68%, respectively, inhibition of phenylquinone writhing. For comparison, aspirin and propoxyphene hydrochloride, known analgesic agents, effect a 34% and 50% inhibition with doses of 60 mg/kg. and 28 mg/kg., respectively. These data demonstrate that compounds of this invention are useful for the alleviation of pain in mammals when administered in doses ranging from 0.2 to about 50 mg per kg. of body weight per day.

The compounds of the present invention may be administered by any convenient route such as orally, intramuscularly, intravenously, subcutaneously, or intraperitoneally. The preferred route of administration is oral, for example, with an inert diluent or with an edible carrier or in gelatin capsules or tablets.

For the purpose of oral therapeutic administration, the active compounds of this invention may be incorporated with excipients and used in the form of tablets, troches, capsules, elixirs, suspensions, syrups, wafers, chewing gum, and the like. These preparations should contain at least 0.5% of active compound, but may be varied depending upon the particular form and may conveniently be between 7% to about 70% of the weight of the unit. The amount of active compound in such compositions is such that a suitable dosage will be obtained. Preferred compositions and preparations according to the present invention are prepared so that an oral dosage unit form contains between 10 and 200 milligrams of active compound.

The tablets, pills, capsules, troches, and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as fatty oil. Other dosage unit forms may contain other various materials which modify the physical form of the dosage unit, for example, as coatings. Thus, tablets or pills may be coated with sugar, shellac, or both. A syrup may contain, in addition to the active compounds, sucrose as a sweetening agent, and certain preservatives, dyes and colorings, and flavors. Materials used in preparing these various compositions must be pharmaceutically pure and non-toxic in the amounts utilized.

The invention is further illustrated by the following examples. Temperatures are given in degrees C.

EXAMPLE 1

1,3-Dihydro-1'-methylspiro[isobenzofuran-1,4'-piperidine]-3-one a. A mixture of 400 g. of o-bromobenzoic acid, 230 g. of thionyl chloride, and 1 ml. of dimethylformamide is heated slowly to reflux, and then for one hour under reflux. The excess thionyl chloride is distilled under reduced pressure, and the residue is dissolved in 1 l. of dichloromethane. The resulting solution is added dropwise with stirring to a solution of 520 g. of 2-amino-2-methylpropanol in 1 l. of dichloromethane cooled to 0°, and the mixture is stirred for 2 hours at 0° and filtered. The solid is air dried, stirred for 1 hour in 2 l. of warm water, filtered again, washed liberally with water, and air dried to an off-white solid, 2-bromo-N-(1-hydroxy-2-methyl-2-propyl)benzamide, m.p. 142°–145°.

b. 254 g. of 2-bromo-N-(1-hydroxy-2-methyl-2-propyl)benzamide are added to 200 ml. of cold (0°) stirred thionyl chloride in the course of 15 minutes. The solution is stirred at 0° for one-half hour and at room temperature for 12 hours, and is then poured into 1.5 l. of ether. The solid which separates is collected, washed with ether, dried, and then added at 0° to 1 l. of 20% aqueous sodium hydroxide. The mixture is extracted with ether, and the ether solution is dried over potassium carbonate and concentrated to an oil. Recrystallization from hexane provides colorless crystals, m.p. 39°–40°, of 2-(2-bromophenyl)-4,4-dimethyl-2-oxazoline.

c. A Grignard reagent is prepared by the dropwise addition of a solution of 34.4 g. of 2-(2-bromophenyl)-4,4-dimethyl-2-oxazoline and 400 ml. of tetrahydrofuran to a refluxing stirred mixture of 4.0 g. of magnesium shavings and 100 ml. of tetrahydrofuran. Initiation with iodine crystals is sometimes required. After addition, the mixture is heated under reflux for 2 hours. Then, 15.8 g. of 1-methyl-4-piperidone are added dropwise in a period of 15 minutes, the solution is heated under reflux for one-half hour and allowed to cool to room temperature. Approximately 12.5 ml. of saturated aqueous ammonium chloride are added dropwise, the mixture is filtered, and the filtrate is extracted with benzene. The benzene solution is dried over potassium carbonate, concentrated, and the residue is recrystallized from ethanol to provide colorless crystals, m.p. 162°–163°, of 4-[2-(4,4-dimethyl-2-oxazolin-2-yl)phenyl]-4-hydroxy-1-methylpiperidine.

d. A solution of 6.0 g. of 4-[2-(4,4-dimethyl-2-oxazolin-2-yl)phenyl]-4-hydroxy-1-methylpiperidine and 70 ml. of 3N hydrochloric acid is heated under reflux for 3 hours, cooled to 0°, and made basic with sodium hydroxide. The mixture is extracted with chloroform, and the chloroform solution is dried over potassium carbonate and concentrated to a solid. Recrystallization from benzene provides colorless crystals, m.p. 147°–148°, of 1,3-dihydro-1'-methylspiro[isobenzofuran-1,4'-piperidine]-3-one.

Analysis: Calc. for $C_{13}H_{15}NO_2$ : C 71.87%; H 6.96%; N 6.45%; Found : C 71.96%; H 7.03%; N 6.54%.

EXAMPLE 2

1'-Butyl-1,3-dihydrospiro]isobenzofuran-1,4'-piperidine]-3-one a. Reaction of 1-butyl-4-piperidone and 2-(2-bromophenyl)-4,4-dimethyl-2-oxazoline by the method described in Example 1c provides yellow crystals, m.p. 80°–82°, of 1-butyl-4-[2-(4,4-dimethyl-2-oxazolin-2-yl)phenyl]-4-hydroxypiperidine.

b. Treatment of 1-butyl-4-[2-(4,4-dimethyl-2-oxazolin-2-yl)phenyl]-4-hydroxypiperidine with hydrochloric acid by the method described in Example 1d provides colorless crystals, m.p. 60°–62°, of 1'-butyl-1,3-dihydrospiro-[isobenzofuran-1,4'-piperidine]-3-one.

Analysis: Calc. for $C_{16}H_{21}NO_2$ : C 74.10; H 8.16; N 5.40; Found : C 73.85; H 8.28; N 5.53.

EXAMPLE 3

1,3-Dihydro-1'-(2-phenethyl)spiro[isobenzofuran-1,4'-piperidine]-3-one a. Reaction of 1-(2-phenethyl)-4-piperidone and 2-(2-bromophenyl)-4,4-dimethyl-2-oxazoline by the method described in Example 1c provides colorless crystals, m.p. 130°–132°, of 4-[2-(4,4-dimethyl-2-oxazolin-2-yl)phenyl]-4-hydroxy-1-(2-phenethyl)-piperidine.

b. Treatment of 4-[2-(4,4-dimethyl-2-oxazolin-2-yl)phenyl]-4-hydroxy-1-(2-phenethyl)piperidine with hydrochloric acid by the method described in Example 1d provides colorless crystals, m.p. 101°–104°, of 1,3- dihydro-1′-(2 -phenethyl)spiro[isobenzofuran-1,4′-piperidine]-3-one.

Analysis: Calc. for $C_{20}H_{21}NO_2$ : C 78.14; H 6.89; N 4.55; Found : C 78.22; H 6.97; N 4.53.

EXAMPLE 4

1,3-Dihydro-5-methoxy-1′-methylspiro[isobenzofuran-1,4′-piperidine]-3-one a. Preparation of 2-bromo-5-methoxybenzoyl chloride and its reaction with 2-amino-2-methylpropanol by the method described in Example 1*a* provides colorless crystals, m.p. 132°–134°, of 2-bromo-N-(1-hydroxy-2-methyl-2-propyl)-5-methoxybenzamide.

b. Reaction of 2-bromo-N-(1-hydroxy-2-methyl-2-propyl)-5-methoxybenzamide and thionyl chloride by the method described in Example 1b provides colorless crystals, m.p. 57°–59°, of 2-(2-bromo-5-methoxyphenyl)-4,4-dimethyl-2-oxazoline.

c. Reaction of 1-methyl-4-piperidone and 2-(2-bromo-5-methoxyphenyl)-4,4-dimethyl-2-oxazoline by the method described in Example 1c provides yellow crystals, m.p. 154°–156°, of 4-[2-(4,4-dimethyl-2-oxazolin-2-yl)-5-methoxyphenyl]-4-hydroxy-1-methylpiperidine.

d. Treatment of 4-[2-(4,4-dimethyl-2-oxazolin-2-yl)-5-methoxyphenyl]-4-hydroxy-1-methylpiperidine with hydrochloric acid by the method described in Example 1*d* provides colorless crystals, m.p. 123°–125°, of 1,3-dihydro-5-methoxy-1′-methylspiro[isobenzofuran-1,4′-piperidine]-3-one.

Analysis: Calc. for $C_{14}H_{17}NO_3$ : C 68.00; H 6.93; N 5.66; Found : C 68.13; H 6.98; N 5.58.

EXAMPLE 5

1,3-Dihydro-1′-[4,4-di(4-fluorophenyl)butyl]-spiro[isobenzofuran-1,4′-piperidine]-3-one a. Reaction of 1-benzyl-4-piperidine and 2-(2-bromophenyl)-4,4-dimethyl-2-oxazoline by the method described in Example 1*c* provides pale yellow crystals, m.p. 109°–112°, of 1-benzyl-4-[2-(4,4-dimethyl-2-oxazolin-2-yl)phenyl]-4-hydroxypiperidine.

b. Treatment of 1-benzyl-4-[2-(4,4-dimethyl-2-oxazolin-2-yl)phenyl]-4-hydroxypiperidine with hydrochloric acid by the method described in Example 1d provides colorless crystals, m.p. 105°–106°, of 1′-1,3-dihydrospiro[isobenzofuran-1,4′-piperidine]-3-one.

c. A mixture of 29 g. of 1′-benzyl-1,3-dihydrospiro[isobenzofuran-1,4′-piperidine]-3-one, 200 ml. of ethanol, 10 ml. of concentrated hydrochloric acid, and 4.5 g. of 10% palladium on charcoal is hydrogenated at 50 p.s.i. and 50°, and then filtered. The filtrate is concentrated to a solid which is dissolved in chloroform. The chloroform solution is washed with aqueous sodium hydroxide, dried over potassium carbonate, and concentrated to a solid. Recrystallization from 2-propanol provides colorless crystals, m.p. 129°–131°, of 1,3-dihydrospiro[isobenzofuran-1,4′-piperidine]-3-one.

d. A mixture of 4.0 g. of 1,3-dihydrospiro[isobenzofuran-1,4′-piperidine]-3-one, 6.4 g. of 4-chloro-1,1-di(4-fluorophenyl)butane, 10 g. of potassium carbonate, and 25 ml. of 1-butanol is heated under reflux for 48 hours and filtered. The filtrate is diluted with water and extracted with benzene. The benzene solution is dried over potassium carbonate and concentrated to an oil, 1,3-dihydro-1′-[4,4-di(4-fluorophenyl)butyl]-spiro[isobenzofuran-1,4′-piperidine]-3-one. The oil is converted to a crystalline hydrochloride salt, m.p. 182°–183° (from benzene).

Analysis: Calc. for $C_{28}H_{27}NO_2.HCl$ : C 69.52; H 5.78; N 2.89; Found : C 69.74; H 5.93; N 2.81.

EXAMPLE 6

1,3-Dihydro-1′-[3-(4-fluorobenzoyl)propyl]-spiro[isobenzofuran-1,4′-piperdine]-3-one A mixture of 4.0 g. of 1,3-dihydrospiro[isobenzofuran-1,4′-piperidine], 6.04 g. of α-chloro-p-fluorobutyrophenone ethylene ketal, 10 g. of potassium carbonate, and 50 ml. of 1-butanol is heated under reflux with stirring for 65 hours, cooled, and filtered. The filtrate is concentrated to an oil wich is dissolved in 50 ml. of ethanol and 50 ml. of 3N hydrochloric acid. After 2 hours, the solution is made basic and extracted with benzene. Concentration of the benzene solution provides 1,3-dihydro-1′-[3-(4-fluorobenzoyl)propyl]-spiro[isobenzofuran-1,4′-piperidine]-3-one as an oil; hydrochloride salt, m.p. 183°–184°.

Analysis: Calc. for $C_{23}H_{26}FNO_2.HCl$ : C65.41; H 5.74; N 3.47; Found : C 65.30; H 5.86; N 3.31.

EXAMPLE 7

1′-(2-Benzoylethyl)-1,3-dibhydrospiro[isobenzofuran-1,4′-piperidine]-3-one

A mixture of 0.8 g. of 1,3-dihydrospiro[isobenzofuran-1,4′-piperidine]-3-one, 5 ml. of dimethylformamide, 0.85 g. of anhydrous sodium carbonate, and 1.28 g. of β-dimethylaminopropiophenone methiodide is stirred at room temperature for 18 hours, diluted with water, and extracted with chloroform. The chloroform solution is dried over sodium sulfate and concentrated to an oil which solidifies. Recrystallization from benzene-hexane provides colorless crystals, m.p. 108°–110°, of 1′-(2-benzoylethyl)-1,3-dihydrospiro[isobenzofuran-1,4′-piperidine]-3-one.

Analysis: Calc. for $C_{21}H_{21}NO_3$ : C 75.19; H 6.32; N 4.18 Found : C 75.30; H 6.32; N 4.18.

EXAMPLE 8

1,3-Dihydro-6-fluoro-1′-methylspiro[isobenzofuran-1,4′-piperidine]-3-one a. Preparation of 2-chloro-4-fluorobenzoyl chloride and its reaction with 2-amino-2-methylpropanol by the method described in Example 1a provides colorless crystals, m.p. 61°–63°, of 2-chloro-4-fluoro-N-(1-hydroxy-2-methyl-2-propyl)benzamide.

b. Reaction of 2-chloro-4-fluoro-N-(1-hydroxy-2-methyl-2-propyl)benzamide and thionyl chloride by the method described in Example 1b provides 2(2-chloro-4-fluorophenyl)-4,4-dimethyl-2-oxazoline as a liquid; hydrochloride salt, m.p. 138°–139°.

c. Reaction of 1-methyl-4-piperidone and 2-(2-chloro-4-fluorophenyl)-4,4-dimethyl-2-oxazoline by the method described in Example 1c provides 4-[2,2-dimethyl-2-oxazolin-2-yl)-5-fluorophenyl]-4-hydroxy-1-methylpiperidine.

d. Treatment of 4-[2-(2,2-dimethyl-2-oxazolin-2-yl)-5-fluorophenyl]-4-hydroxy-1-methylpiperidine with hydrochloric acid by the method described in Example 1*d* provides 1,3-dihydro-6-fluoro-1′-methylspiro[isobenzofuran-1,4′-piperidine]-3-one.

EXAMPLE 9

1,3-Dihydro-5,6-dimethoxy-1'-[3-(4-fluorobenzoyl)-propyl]-spiro[isobenzofuran-1,4'-piperidine]-3-one a. Preparation of 2-bromo-4,5-dimethoxybenzoyl chloride and its reaction with 2-amino-2-methyl-propanol by the method described in Example 1a provides colorless crystals, m.p. 106°–108°, of 2-bromo-4,5-dimethoxy-N-(1-hydroxy-2-methyl-2-propyl)benzamide.

b. Reaction of 2-bromo-4,5-dimethoxy-N-(1-hydroxy-2-methyl-2-propyl)benzamide and thionyl chloride by the method described in Example 1b provides 2-(2-bromo-4,5-dimethoxyphenyl)-4,4-dimethyl-2-oxazoline as colorless crystals, m.p. 49°–51°.

c. Reaction of 1-benzyl-4-piperidine and 2-(2-bromo-4,5-dimethoxyphenyl)-4,4-dimethyl-2-oxazoline by the method described in Example 1c provides 1'-benzyl-1,3-dihydro-5,6-dimethoxyspiro[isobenzofuran-1,4'-piperidine]-3-one as an oil.

d. Treatment of 1-benzyl-4-[4,5-dimethoxy-2-(4,4-dimethyl-2-oxazolin-2-yl)phenyl]-4-hydroxypiperidine with hydrochloric acid by the method described in Example 1d provides colorless crystals, m.p. 143°–144°, of 1'-benzyl-1,3-dihydro-5,6-dimethoxyspiro[isobenzofuran-1,4'-piperidine]-3-one.

e. Hydrogenation of 1'-benzyl-1,3-dihydro-5,6-dimethoxyspiro[isobenzofuran-1,4'-piperidine]-3-one by the method described in Example 5*c* provides 1,3-dihydro-5,6-dimethoxyspiro[isobenzofuran-1,4'-piperidine]-3-one.

f. Reaction of 1,3-dihydro-5,6-dimethoxyspiro-[isobenzofuran-1,4'-piperidine]-3-one and αchloro-p-fluorobutyrophenone fluorobutyrophenone ethylene ketal by the method described in Example 6 provides 1,3-dihydro-5,6-dimethoxy-1'-[3-(4-fluorobenzoyl)-propyl]spiro[isobenzofuran-1,4'-piperidine]-3-one.

EXAMPLE 10

1,3-Dihydro-1'-methyl-5,6-methylenedioxyspiro[isobenzofuran-1,4'-piperidine]-3-one a. Preparation of 2-bromo-4,5-methylenedioxybenzoyl chloride and its reaction with 2-amino-2-methyl-propanol by the method described in Example 1a provides colorless crystals, m.p. 114°–116°, of 2bromo-N-(1-hydroxy-2-methyl-2-propyl)-4,5-methylenedioxybenzamide.

b. Reaction of 2-bromo-N-(1-hydroxy-2-methyl-2-propyl)-4,5-methylenedioxybenzamide and thionyl chloride by the method described in Example 1b provides colorless crystals, m.p. 58.5°–60°, of 2-(2-bromo-4,5-methylenedioxyphenyl)-4,4-dimethyl-2-oxazoline.

c. Reaction of 2-(2-bromo-4,5-methylenedioxyphenyl)-4,4-dimethyl-2-oxazoline and 1methyl-4-piperidone by the method described in Example 1c provides 4-[2-(4,4-dimethyl-2-oxazolin-2-yl)-4,5-methylenedioxyphenyl]-4-hydroxy-1-methylpiperidine.

d. Treatment of 4-[2-(4,4-dimethyl-2-oxazolin-2-yl)-4,5-methylenedioxyphenyl]-4-hydroxy-1-methylpiperidine with hydrochloric acid by the method described in Example 1d provides 1,3-dihydro-1'-methyl-5,6-methylenedioxyspiro-[isobenzofuran-1,4'-piperidine]-3-one.

EXAMPLE 11

1'-Allyl-1,3-dihydrospiro[isobenzofuran-1,4'-piperidine]-3-one

A mixture of 1.02 g. of 1,3-dihydrospiro[isobenzofuran-1,4'-piperidine]-3-one, 1.0 g. of sodium bicarbonate, 10 ml. of chloroform, and 0.60 g. of allyl bromide is stirred at room temperature for 24 hours and filtered. The filtrate is washed with water, dried over potassium carbonate, and concentrated to an oily solid.

EXAMPLE 12

1,3-Dihydro-1'-(3-methyl-2-butenyl)spiro[isobenzofuran-1,4'-piperidine]-3-one

Reaction of 1,3-dihydrospiro[isobenzofuran-1,4'-piperidine]-3-one and 1-bromo-3-methyl-2-butene by the method described in Example 11 provides an oil, hydrochloride salt, m.p. 255°–257°.

Analysis: Calc. for $C_{17}H_{21}NO_2.HCl$ : C 66.33; H 7.21; N 4.55; Found : C 66.52; H 7.34; N 4.77.

EXAMPLE 13

1,3-Dihydro-1'-[3-(4-fluorobenzoyl)propyl]-spiro[isobenzofuran-1,3'-pyrrolidine]-3-one a. Reaction of 1-benzyl-3-pyrrolidone and 2-(2-bromophenyl)-4,4-dimethyl-2-oxazoline by the method described in Example 1*c* provides 1-benzyl-3-[2-(4,4-dimethyl-2-oxazolin-2-yl)phenyl]-3-hydroxypyrrolidine as an oil.

b. Treatment of 1-benzyl-3-[2-(4,4-dimethyl-2-oxazolin-2-yl)phenyl]-3-hydroxypyrrolidine with hydrochloric acid by the method described in Example 1d provides colorless crystals, m.p. 101°-102°, of 1'-benzyl-1,3-dihydrospiro[isobenzofuran-1,3'-pyrrolidine]-3-one c. Hydrogenation of 1'-benzyl-1,3-dihydrospiro[isobenzofuran-1,3'-pyrrolidine]-3-one by the method described in Example 5c provides 1,3-dihydrospiro[isobenzofuran-1,3'-pyrrolidine]-3-one.

d. Reaction of 1,3-dihydrospiro[isobenzofuran1,3'-pyrrolidine]-3-one and α-chloro-p-fluorobutyrophenone ethylene ketal by the method described in Example 6 provides 1,3-dihydro-1'-[3-(4-fluorobenzoyl)-propyl]spiro[isobenzofuran-1,3'-piperidine]-3-one.

EXAMPLE 14

1,3-Dihydro-1'-[3-(4-fluorobenzoyl)propyl]-spiro[isobenzofuran-1,3'-piperidine]-3-one a. Reaction of 1-benzyl-3-piperidone and 2-(2-bromophenyl)-4,4-dimethyl-2-oxazoline by the method described in Example 1c provides off-white crystals, m.p. 117°–118°, of 1-benzyl-3-[2-(4,4-dimethyl-2-oxazolin-2-yl)phenyl]-3-hydroxypiperidine.

b. Treatment of 1-benzyl-3-[2-(4,4-dimethyl-2-oxazolin-2-yl)phenyl]-3-hydroxypiperidine with hydrochloric acid by the method described in Example 1*d* provides colorless crystals, m.p. 71°–73°, of 1'-benzyl-1,3-dihydrospiro[isobenzofuran-1,3'-piperidine]-3-one.

c. Hydrogenation of 1'-benzyl-1,3-dihydrospiro[isobenzofuran-1,3'-piperidine]-3-one by the method described in Example 5*c* provides 1,3-dihydrospiro[isobenzofuran-1,3'-piperidine]-3-one.

d. Reaction of 1,3-dihydrospiro[isobenzofuran-1,3'-piperidine]-3-one with α-chloro-p-fluorobutyrophenone ethylene ketal by the method described in Example 6 provides 1,3-dihydro-1'-[3-(4-fluorobenzoyl)-propyl]spiro[isobenzofuran-1,3'-piperidine]-3-one.

EXAMPLE 15

1'-Methyl-1,2',3,3',4',5',6',7'-octohydrospiro[isobenzofuran-1,4'-azepine]-3-one a. Reaction of 2,3,4,5,6,7-hexahydro-1-methylazepin-4-one and 2-(2-bromophenyl)-4,4-dimethyl-2-oxazoline by the method described in Example 1c provides 4-[2-(4,4-dimethyl-2-oxazolin-2-yl)phenyl]-2,3,4,5,6,7-hexahydro-4-hydroxy-1-methylazepine.

b. Treatment of 4-[2-(4,4-dimethyl-2-oxazolin-2-yl)phenyl]-2,3,4,5,6,7-hexahydro-4-hydroxy-1-methylazepine with hydrochloric acid by the method described in Example 1*d* provides 1'-methyl-1,2',3,3',-4',5',6',7'-octahydrospiro[isobenzofuran-1,4'-azepine]-3-one.

EXAMPLE 16

1,3-Dihydro-1'-methylspiro[isobenzofuran-1,4'-piperidine]

a. To a cold (−20°) solution of 1.87 g. o-bromobenzyl alcohol, 15 ml. of dry tetrahydrofuran, and 5 ml. of hexane is added dropwise with stirring during 15 min. 5 ml. of 2.0 N n-butyllithium in hexane. The mixture is stirred for 1 hour, and a solution of 1.25 g. of 1-methyl-4-piperidone in 5 ml. of tetrahydrofuran is added dropwise. After 2 hours, the mixture is diluted with aqueous ammonium chloride and extracted with chloroform. The chloroform solution is dried over potassium carbonate and concentrated to a solid. Recrystallization from benzene provides colorless crystals, m.p. 118°–119°, of 4-hydroxy-4-(α-hydroxy-2-tolyl)-1-methylpiperidine.

b. To a stirred suspension of 0.30 g. of lithium aluminum hydride and 20 ml. of tetrahydrofuran is added dropwise during 15 min. a solution of 1,3-dihydro-1'-methylspiro[isobenzofuran-1,4'-piperidine]-3-one. The mixture is stirred at room temperature for one-half hour and at 50° for 1 hour, cooled, diluted cautiously with water, and extracted with chloroform. The chloroform solution is dried over potassium carbonate and concentrated to a solid. Recrystallization from benzene provides colorless crystals, m.p. 118°–119°, of 4-hydroxy-4-(α-hydroxy-2-tolyl)-1-methylpiperidine.

c. A solution of 5.8 g. of 1'-benzyl-1,3-dihydrospiro[isobenzofuran-1,4'-piperidine]-3-one, 40 ml. of benzene, and 2.5 ml. of ethyl chloroformate is heated under reflux for 18 hours and concentrated to a solid. Recrystallization from benzene-cyclohexane provides colorless crystals, m.p. 150°–151°, of 1,3-dihydro-1'-ethoxycarbonylspiro[isobenzofuran-1,4'-piperidine]-3-one. Reduction with lithium aluminum hydride by the method described in Example 16*b* provides 4-hydroxy-4-(α-hydroxy-2-tolyl)-1-methylpiperidine, m.p. 118°–119°.

d. A solution of 2.0 g. of 4-hydroxy-4-(α-hydroxy-2-tolyl)-1-methylpiperidine, 15 ml. of acetic acid and 3 ml. of conc. hydrochloric acid is heated at 110° for 10 min., cooled, diluted with water, made basic with sodium hydroxide, and extracted with chloroform. The chloroform solution is dried over potassium carbonate and concentrated to a solid. Recrystallization from hexane provides colorless crystals, m.p. 76°–77°, of 1,3-dihydro-1'-methylspiro[isobenzofuran-1,4'-piperidine].

EXAMPLE 17

1'-Cyclopropylmethyl-1,3-dihydrospiro[isobenzofuran-1,4'-piperidine]

a. To a cold stirred solution of 2.03 g. of 1,3-dihydrospiro[isobenzofuran-1,4'-piperidine] and 1.2 g. of triethylamine in 25 ml. of chloroform is added dropwise a solution of 1.2 g. of cyclopropylcarbonyl chloride in 5 ml. of chloroform. After 3 hours, the solution is washed with water, dried over potassium carbonate, and concentrated to a solid. Recrystallization from 2-propanol provides colorless crystals, m.p. 174°–175°, of 1'-cyclopropylcarbonyl-1,3-dihydrospiro[isobenzofuran-1,4'-piperidine]-3-one.

b. Reduction of 1'-cyclopropylcarbonyl-1,3-dihydrospiro[isobenzofuran-1,4'-piperidine]-3-one with lithium aluminum hydride by the method described in Example 16*b* provides colorless crystals, m.p. 156°–157°, of 1-cyclopropylmethyl-4-hydroxy-4-(α-hydroxy-2-tolyl)piperidine.

c. Treatment of 1-cyclopropylmethyl-4-hydroxy-4-(α-hydroxy-2-tolyl)piperidine with hydrochloric acid by the method described in Example 16*d* provides 1'-cyclopropylmethyl-1,3-dihydrospiro[isobenzofuran-1,4'-piperidine] as an oil (hydrochloride salt, m.p. 222°–224°).

Analysis: Calc. for $C_{16}H_{21}NO.HCl$ : C 68.68; H 7.93; N 5.01; Found : C 68.51; H 7.92; N 4.90.

EXAMPLE 18

1,3-Dihydro-1'-[3-(4-fluorobenzoyl)propyl]-spiro[isobenzofuran-1,4'-piperidine]

a. Reduction of 1'-benzyl-1,3-dihydrospiro[isobenzofuran-1,4'-piperidine]-3-one with lithium aluminum hydride by the method described in Example 16*b* provides colorless crystals, m.p. 128°–129°, of 1-benzyl-4-hydroxy-4-(α-hydroxy-2-tolyl)piperidine.

b. Acid treatment of 1-benzyl-4-hydroxy-4-(α-hydroxy-2-tolyl)]piperidine by the method described in Example 16*d* provides 1'-benzyl-1,3-dihydrospiro[isobenzofuran-1,4'-piperidine] as colorless crystals, m.p. 67°–68.5°.

c. Reaction of 1'-benzyl-1,3-dihydrospiro[isobenzofuran-1,4'-piperidine] and ethyl chloroformate by the method described in Example 16c provides colorless crystals, m.p. 57.5°–58.5°, of 1,3-dihydro-1'-ethoxycarbonylspiro[isobenzofuran-1,4'-piperidine].

d. A solution of 7.0 g. of 1,3-dihydro-1'-ethoxycarbonylspiro[isobenzofuran-1,4°-piperidine], 100 ml. of ethanol, and 250 ml. of 20% aqueous potassium hydroxide is heated under reflux for 12 hours, cooled, concentrated to 300 ml., diluted with water, and extracted with chloroform. The chloroform solution is dried over potassium carbonate and concentrated to a solid. Recrystallization from hexane provides colorless crystals, m.p. 84°–85.5°, of 1,3-dihydrospiro[isobenzofuran-1,4'-piperidine].

e. Reaction of 1,3-dihydrospiro[isobenzofuran-1,4'-piperidine] and α-chloro-p-fluorobutyrophenone ethylene ketal by the method described in Example 6 provides 1,3-dihydro-1'-[3-(4-fluorobenzoyl)propyl]-spiro[isobenzofuran-1,4'-piperidine] as a solid, hydrochloride salt, m.p. 215°–217°.

Analysis: Calc. for $C_{21}H_{24}FNO_2.HCl$ : C 67.77; H 6.47; N 3.59; Found : C 68.15; H 6.40; N 3.46.

EXAMPLE 19

1,3-Dihydro-1'-[4,4-di(4-fluorophenyl)butyl]-spiro[isobenzofuran-1,4'-piperidine] hydrochloride Reaction of 1,3-dihydrospiro[isobenzofuran-1,4'-piperidine] and 4-chloro-1,1-di(4-fluorophenyl)butane by the method described in Example 5d provides colorless crystals, m.p. 210°–213°, of 1,3-dihydro-1'-[4,4-di(4-fluorophenyl)butyl]spiro[isobenzofuran-1,4'-piperidine]hydrochloride.

Analysis: Calc. for $C_{28}H_{29}F_2NO.HCl$ : C 71.55; H 6.43; N 2.98; Found : C 71.35; H 6.32; N 2.89.

EXAMPLE 20

1,3-Dihydro-1'-acetylspiro[isobenzofuran-1,4'-piperidine]

a. Reaction of 1,3-dihydrospiro[isobenzofuran-1,4'-piperidine]-3-one and acetyl chloride by the method described in Example 17a provides colorless crystals, m.p. 210°–211°, of 1'-acetyl-1,3-dihydrospiro[isobenzofuran-1,4'-piperidine]-3-one.

b. Reduction of 1'-acetyl-1,3-dihydrospiro[isobenzofuran-1,4'-piperidine]-3-one with lithium aluminum hydride by the method described in Example 16b provides colorless crystals, m.p. 116°–117°, of 1-ethyl-4-hydroxy-4-(α-hydroxy-2-tolyl)piperidine.

c. Treatment of 1-ethyl-4-hydroxy-4-(α-hydroxy-2-tolyl)piperidine with formic acid by the method described in Example 17c provides 1,3-dihydro-1'-ethylspiro[isobenzofuran-1,4'-piperidine] as an oil.

EXAMPLE 21

1,3-Dihydro-1'-methyl-6-trifluoromethylspiro[isobenzofuran-1,4'-piperidine]

a. Reaction of 2-bromo-4-trifluoromethylbenzyl alcohol and 1-methyl-4-piperidone by the method described in Example 16*a* provides 4-hydroxy-4-(α-hydroxy-4-trifluoromethyl-2-tolyl)-1-methylpiperidine.

b. Treatment of 4-hydroxy-4-(α-hydroxy-4-trifluoromethyl-2-tolyl)-1-methylpiperidine with hydrochloric acid by the method described in Example 16*d* provides 1,3-dihydro-1'-methyl-6-trifluoromethylspiro[isobenzofuran-1,4'-piperidine].

EXAMPLE 22

1,3-Dihydro-1',5-dimethylspiro[isobenzofuran-1,4'-piperidine]

a. Reaction of 2-bromo-5-methylbenzyl alcohol and 1-methyl-4-piperidone by the method described in Example 16*a* provides 4-hydroxy-4-(α-hydroxy-5-methyl-2-tolyl)-1-methylpiperidine.

b. Treatment of 4-hydroxy-4-(α-hydroxy-5-methyl-2-tolyl)-1-methylpiperidine with hydrochloric acid by the method described in Example 16*d* provides 1,3-dihydro-1',5-dimethylspiro[isobenzofuran-1,4'-piperidine].

EXAMPLE 23

6-Chloro-1,3-dihydro-1'-methylspiro[isobenzofuran-1,4'-piperidine]

a. Reaction of 2-bromo-4-chlorobenzyl alcohol and 1-methyl-4-piperidone by the method described in Example 16*a* provides 4-(4-chloro-α-hydroxy-2-tolyl)-4-hydroxy-1-methylpiperidine.

b. Treatment of 4-(4-chloro-α-hydroxy-2-tolyl)-4-hydroxy-1-methylpiperidine with hydrochloric acid by the method described in Example 16*d* provides 6-chloro-1,3-dihydro-1'-methylspiro[isobenzofuran-1,4'-piperidine].

EXAMPLE 24

1,3-Dihydro-5-fluoro-1'-methylspiro[isobenzofuran-1,4'-piperidine]

a. Reaction of 2-bromo-5-fluorobenzyl alcohol and 1-methyl-4-piperidone by the method described in Example 16*a* provides 4-(5-fluoro-α-hydroxy-2-tolyl)-4-hydroxy-1-methylpiperidine.

b. Treatment of 4-(5-fluoro-α-hydroxy-2-tolyl)-4-hydroxy-1-methylpiperidine with hydrochloric acid by the method described in Example 16*d* provides 1,3-dihydro-5-fluoro-1'-methylspiro[isobenzofuran-1,4'-piperidine].

EXAMPLE 25

1,3-Dihydro-1'-methylspiro[isobenzofuran-1,3'-pyrrolidine]

a. Reaction of o-bromobenzyl alcohol and 1-methyl-3-pyrrolidone by the method described in Example 16*a* provides 3-hydroxy-3-(α-hydroxy-2-tolyl)-1-methylpyrrolidine.

b. Treatment of 3-hydroxy-3-(α-hydroxy-2-tolyl)-1-methylpyrrolidine with hydrochloric acid by the method described in Example 16*d* provides 1,3-dihydro-1'-methylspiro[isobenzofuran-1,3'-pyrrolidine].

EXAMPLE 26

1,3-Dihydro-5-hydroxy-1'-methylspiro[isobenzofuran-1,4'-piperidine]-3-one

Treatment of 1,3-dihydro-5-methoxy-1'-methylspiro[isobenzofuran-1,4'-piperidine]-3-one with 48% hydrobromic acid provides 1,3-dihydro-5-hydroxy-1'-methylspiro[isobenzofuran-1,4'-piperidine]-3-one.

EXAMPLE 27

1,3-Dihydro-1'-(3-hydroxy-3-phenylpropyl)-spiro[isobenzofuran-1,4'-piperidine]-3-one A solution of 2.5 g. of 1'-(2-benzoylethyl)-1,3-dihydrospiro[isobenzofuran-1,4'-piperidine]-3-one, 30 ml. of methanol, 10 ml. of tetrahydrofuran, and 0.35 g. of sodium borohydride is stirred for 4 hours, diluted with water, and extracted with chloroform. The chloroform solution is dried over sodium sulfate and concentrated to a solid. Recrystallization from benzene yields colorless crystals, m.p. 144°–146°.

Analysis: Calc. for $C_{21}H_{23}NO_3$ : C 74.74; H 6.88; N 4.15; Found : C 74.84; H 7.09; N 4.26.

EXAMPLE 28

1'-(2-Benzhydryloxyethyl)-1,3-dihydrospiro[isobenzofuran-1,4'-piperidine]-3-one

Reaction of 1,3-dihydrospiro[isobenzofuran-1,4'-piperidine]-3-one and 2-benzhydryloxy-1-chloroethane by the method described in Example 5*d* provides 1'-(2-benzhydryloxyethyl)-1,3-dihydrospiro[isobenzofuran-1,4'-piperidine]-3-one as colorless crystals, m.p. 99°–100°.

Analysis: Calc. for $C_{27}H_{27}NO_3$ : C 78.42; H 6.58; N 3.39; Found : C 78.34; H 6.60; N 3.37.

We claim:

1. Process for the preparation of a compound of the formula

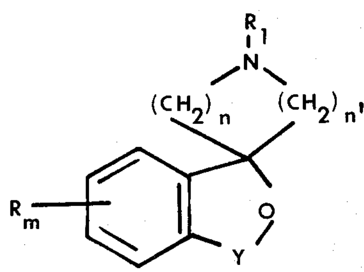

in which

R is hydrogen, alkyl of 1 to 6 carbon atoms, alkoxy of 1 to 6 carbon atoms, trifluoromethyl, halogen, hydroxy or methylenedioxy;

$R_1$ is alkyl of 1 to 6 carbon atoms, cycloalkylalkyl of 4 to 8 carbon atoms, alkenyl of 3 to 6 carbon atoms, phenylalkyl of the formula $CH_2(CH_2)_nPhR$, diphenylalkyl of the formula $(CH_2)_nCH(PhR)_2$, diphenylmethoxyalkyl of the formula $(CH_2)_nOCHPh_2$, alkanoyl of 2 to 6 carbon atoms, phenylalkanoyl of the formula $CO(CH_2)_nPhR$, benzoylalkyl of the formula $(CH_2)_nCOPhR$, phenylhydroxyalkyl of the formula $(CH_2)_nCHOHPhR$ or cycloalkylcarbonyl of 4 to 8 carbon atoms;

Y is $CH_2$ C=O;

Ph is phenyl;

*m* is 1 or 2; and

*n* and *n'* are integers from 1 to 3, the sum of *n* and *n'* being from 3 to 5; and the pharmaceutically acceptable acid addition salts thereof, which comprises reacting an o-halobenzoyl chloride with 2-amino-2-methyl-1-propanol to form the corresponding o-halo-N-(1-hydroxy-2-methyl-2-propyl)benzamide, cyclizing said benzamide to the corresponding o-halophenyloxazoline by treatment with a dehydrating agent, converting said oxazoline to a Grignard reagent by reaction with magnesium, reacting said Grignard reagent with a cycloazalkanone to prepare the corresponding hydroxyoxazolinylphenylcycloazalkane, and reacting said azalkane with an acid to form the corresponding 1,3-dihydrospiro[isobenzofuran-cycloazalkane]-3-one.

2. The compound 1,3-dihydro-1'-[4,4-di(4-fluorophenyl)butyl]spiro[isobenzofuran-1,4'-piperidine]-3-one.

3. The compound 1,3-dihydro-1'-[3-(4-fluorobenzoyl)propyl]spiro[isobenzofuran-1,4'-piperidine]-3-one.

4. The compound 1,3-dihydro-1'-[3-(4-fluorobenzoyl)propyl]spiro[isobenzofuran-1,4'-piperidine].

5. The compound 1, 3-dihydro-1'-[3-(4-fluorobenzoyl) propyl]spiro [isobenzofuran-1,3'-pyrrolidine]-3-one.

6. The compound 1'-(2-benzoylethyl)-1,3-dihydrospiro-[isobenzofuran-1,4'-piperidine]-3-one.

* * * * *

UNITED STATES PATENT AND TRADEMARK OFFICE

CERTIFICATE OF CORRECTION

PATENT NO. : 3,962,259

DATED : June 8, 1976

INVENTOR(S) : Bauer et al.

It is certified that error appears in the above-identified patent and that said Letters Patent are hereby corrected as shown below:

Column 2, line 7, change "benzoyalkyl" to --benzoylalkyl--;

Column 3, line 1, change "EXAMPLE B" to --Method B--;

line 4, change "...3one" to --...3-one--;

Column 6, line 40, change "...spiro]iso..." to --spiro[iso...--;

Column 7, line 1, change "...(2 -phenethyl..." to --...(2-phenethyl...--;

line 46, change "1'-1,3-dihydro..." to --1'-benzyl-1,3-dihydro...--;

Column 8, line 16, change "wich" to --which--;

line 27, change "...1,3-dibhydro..." to --...1,3-dihydro...--;

line 56, change "2(2-..." to --2-(2-...--;

line 61, change "4-[2,2-..." to --4-[2-(2,2-...--;

Column 9, line 4, change "...propyl]-spiro..." to --...propyl]spiro...--;

line 35, change "αchloro-..." to --α-chloro...--;

line 36, delete "fluorobutyrophenone" (second occurrence);

UNITED STATES PATENT AND TRADEMARK OFFICE

CERTIFICATE OF CORRECTION

PATENT NO. : 3,962,259

DATED : June 8, 1976

INVENTOR(S) : Bauer et al.

It is certified that error appears in the above-identified patent and that said Letters Patent are hereby corrected as shown below:

Column 9, line 48, change "2bromo..." to --2-bromo...--;

line 58, change "lmethyl..." to --1-methyl...--;

Column 10, line 42, change "...furanl,3'-..." to --...furan-1,3'-...--;

line 46, change "...piperidine..." to --...pyrrolidine...--

Column 11, line 5, change "...octo..." to --...octa...--;

Column 12, line 42, change "...tolyl)]piperidine" to --...tolyl)piperidine--;

line 52, change "...-1,4°-..." to --...-1,4'...--;

Column 15, line 31, change "$CH_2C=O$" to --$CH_2$ or C=O--;

In the Drawing Figure, Formula IX, correct the illegible matter above "N" to read --$R_1$-- and change "$CH_2R$'" to --$CH_2OR$'--.

Signed and Sealed this

Second Day of November 1976

[SEAL]

*Attest:*

RUTH C. MASON
*Attesting Officer*

C. MARSHALL DANN
*Commissioner of Patents and Trademarks*